United States Patent
Miyasato et al.

(10) Patent No.: US 10,476,108 B2
(45) Date of Patent: Nov. 12, 2019

(54) NON-AQUEOUS ELECTROLYTE SOLUTION FOR SECONDARY BATTERY, AND SECONDARY BATTERY

(71) Applicants: MITSUI CHEMICALS, INC., Minato-ku, Tokyo (JP); GS YUASA INTERNATIONAL LTD., Kyoto-shi, Kyoto (JP)

(72) Inventors: Masataka Miyasato, Sodegaura (JP); Takashi Hayashi, Ichihara (JP); Satoko Fujiyama, Kisarazu (JP); Akira Kishimoto, Kyoto (JP); Hiroe Nakagawa, Kyoto (JP)

(73) Assignees: MITSUI CHEMICALS, INC., Minato-Ku, Tokyo (JP); GS YUASA INTERNATIONAL LTD., Kyoto-Shi, Kyoto (JP)

(*) Notice: Subject to any disclaimer, the term of this patent is extended or adjusted under 35 U.S.C. 154(b) by 15 days.

(21) Appl. No.: 15/771,181

(22) PCT Filed: Nov. 2, 2016

(86) PCT No.: PCT/JP2016/082695
§ 371 (c)(1),
(2) Date: Apr. 26, 2018

(87) PCT Pub. No.: WO2017/078107
PCT Pub. Date: May 11, 2017

(65) Prior Publication Data
US 2018/0233777 A1    Aug. 16, 2018

(30) Foreign Application Priority Data
Nov. 5, 2015    (JP) ................. 2015-217704

(51) Int. Cl.
| | |
|---|---|
| H01M 6/04 | (2006.01) |
| H01M 10/0567 | (2010.01) |
| C07F 5/04 | (2006.01) |
| H01M 10/0525 | (2010.01) |

(52) U.S. Cl.
CPC .......... *H01M 10/0567* (2013.01); *C07F 5/04* (2013.01); *H01M 10/0525* (2013.01); *H01M 2300/0025* (2013.01)

(58) Field of Classification Search
CPC ........ H01M 10/0567; H01M 10/0566; H01M 10/0564; H01M 10/0569; H01M 10/056; H01M 10/0525; H01M 10/052; H01M 2300/0025; H01M 2300/028; C07F 5/04
See application file for complete search history.

(56) References Cited

U.S. PATENT DOCUMENTS

| | | | | |
|---|---|---|---|---|
| 7,754,380 | B2* | 7/2010 | Abe | H01M 10/052 |
| | | | | 252/62.2 |
| 2013/0004840 | A1* | 1/2013 | Yu | C07F 9/65746 |
| | | | | 429/203 |
| 2015/0194665 | A1* | 7/2015 | Ohtsuka | H01M 4/137 |
| | | | | 429/188 |
| 2016/0013516 | A1* | 1/2016 | Heishi | H01M 10/0567 |
| | | | | 429/331 |

FOREIGN PATENT DOCUMENTS

| | | |
|---|---|---|
| EP | 2 827 430 A1 | 1/2015 |
| JP | H-09-120825 A | 5/1997 |
| JP | H-10-223258 A | 8/1998 |
| JP | H-11-054133 A | 2/1999 |
| JP | H-11-121033 A | 4/1999 |
| JP | 2002-025609 A | 1/2002 |
| JP | 2002-216844 A | 8/2002 |

(Continued)

OTHER PUBLICATIONS

International Search Report (PCT/ISA/210) dated Jan. 17, 2017, by the Japan Patent Office as the International Searching Authority for International Application No. PCT/JP2016/082695.
Written Opinion (PCT/ISA/237) dated Jan. 17, 2017, by the Japan Patent Office as the International Searching Authority for International Application No. PCT/JP2016/082695.
Rapta et al., "Anion Radicals as Intermediates in the Cathodic Reduction of β-Diketoboronates", Cyclic Voltammetry, EPR and UV-VIS, Electrochimica Acta, vol. 39, No. 15, pp. 2251-2259, 1994.

(Continued)

*Primary Examiner* — Raymond Alejandro
(74) *Attorney, Agent, or Firm* — Buchanan, Ingersoll & Rooney PC

(57) ABSTRACT

A non-aqueous electrolyte solution for a secondary battery, including a boron compound represented by Formula (1). In Formula (1), R represents an alkyl group having from 1 to 12 carbon atoms, an alkenyl group having from 2 to 12 carbon atoms, or a group represented by Formula (2). In Formula (2), each of $R^1$ to $R^3$ independently represents a hydrogen atom, a halogen atom, an alkyl group having from 1 to 12 carbon atoms, an alkenyl group having from 2 to 12 carbon atoms, or an aryl group having from 6 to 12 carbon atoms, and * represents a bonding site with an oxygen atom in Formula (1).

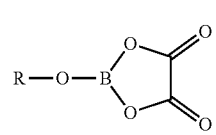

Formula (1)

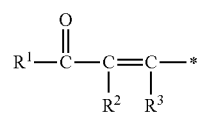

Formula (2)

8 Claims, 2 Drawing Sheets

(56) References Cited

FOREIGN PATENT DOCUMENTS

| JP | 2003-132946 A | 5/2003 |
| JP | 2003-168476 A | 6/2003 |
| JP | 2006-147288 A | 6/2006 |
| JP | 2008-198542 A | 8/2008 |
| JP | 2009-245829 A | 10/2009 |
| WO | WO 2011/024420 A1 | 3/2011 |

OTHER PUBLICATIONS

Heimann et al., "Boron Complexes of β-diketones and Carboxylic Acids. Boric Acid-Catalyzed Pyrone Formation from Fatty Acids", Chemische Berichte, 68(6), pp. 1949-1955, 1965 (abstract) CAplus [online], US: American Chemical Society [retrieved on Jan. 5, 2017], Retrieved from: STN, Accession No. 1965:438976, entire text.

\* cited by examiner

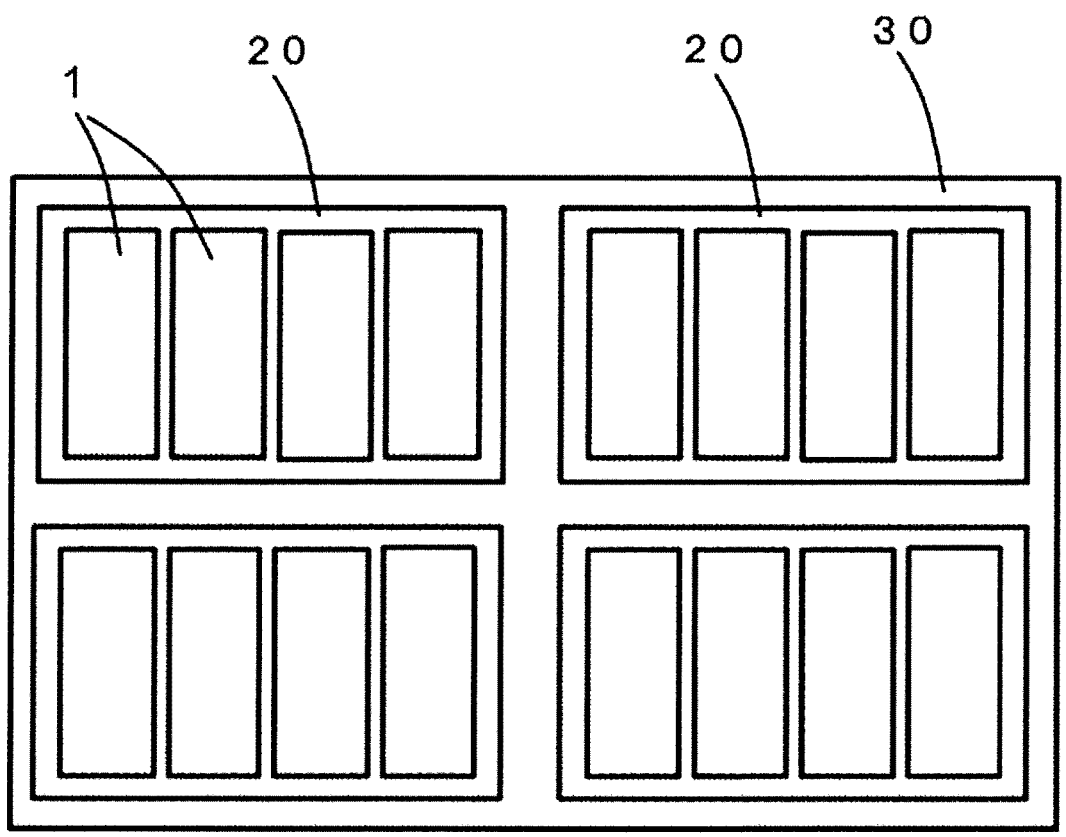

NON-AQUEOUS ELECTROLYTE SOLUTION FOR SECONDARY BATTERY, AND SECONDARY BATTERY

TECHNICAL FIELD

The present invention relates to a non-aqueous electrolyte solution for a secondary battery, and a secondary battery.

BACKGROUND ART

Secondary batteries using a non-aqueous electrolyte solution are widely used as power sources for consumer electronic devices because such batteries have high voltage, high energy density, and high reliability of storage characteristics or the like. Secondary batteries using a non-aqueous electrolyte solution are beginning to be used also as batteries for electric power storage, and automobiles such as electric vehicles (EVs), hybrid vehicles (HEVs), and plug-in hybrid vehicles (PHEVs). Representative examples of secondary batteries using a non-aqueous electrolyte solution include lithium batteries and lithium ion secondary batteries.

The non-aqueous electrolyte solution used in such secondary batteries is a solution obtained by mixing an electrolyte into a non-aqueous solvent, and the electrolyte contained in the non-aqueous electrolyte solution transfers ions between a positive electrode and a negative electrode. The non-aqueous electrolyte solution is demanded to have the following characteristics in order to enhance battery performance of secondary batteries.

First, the non-aqueous electrolyte solution needs to be chemically and electrochemically stable with respect to the positive electrode and the negative electrode in order to improve the storage characteristics and cycle characteristics of secondary batteries.

In order to enhance the charge and discharge characteristics of secondary batteries, the non-aqueous electrolyte solution is preferably a liquid having a high ion movement speed, and specifically, is demanded to have a low viscosity and to be a liquid that readily causes mass transfer by diffusion.

It is known that a carbonate solvent having a high dielectric constant such as propylene carbonate or ethylene carbonate, or a carbonate solvent with low viscosity such as diethyl carbonate, ethyl methyl carbonate, or dimethyl carbonate is used as the non-aqueous solvent of the non-aqueous electrolyte solution in order to satisfy the above characteristics needed for the non-aqueous electrolyte solution. Further, it is known that a boron compound is added to a non-aqueous electrolyte solution to improve battery performance such as storage characteristics, cycle characteristics, or charge and discharge characteristics of a secondary battery (for example, Patent Documents 1 to 10).

Patent Document 1: Japanese Patent Application Laid-Open (JP-A) No. H09-120825
Patent Document 2: JP-A No. H10-223258
Patent Document 3: JP-A No. H11-054133
Patent Document 4: JP-A No. H11-121033
Patent Document 5: JP-A No. 2002-025609
Patent Document 6: JP-A No. 2002-216844
Patent Document 7: JP-A No. 2003-132946
Patent Document 8: JP-A No. 2003-168476
Patent Document 9: JP-A No. 2008-198542
Patent Document 10: JP-A No. 2009-245829

SUMMARY OF INVENTION

Problem to be Solved by the Invention

As disclosed in Patent Documents 1 to 10, addition of a boron compound to a non-aqueous electrolyte solution in order to improve battery performance of a secondary battery is known, and further improvement in battery performance is demanded. In particular, in a secondary battery used as a battery for an automobile such as an EV, an HEV, or a PHEV, an electric motor is driven by discharging electric power accumulated in the secondary battery, and instantaneous discharge with a large current is necessary at the time of starting or accelerating the automobile. In other words, excellent output characteristics are demanded. However, when the DC resistance of the secondary battery is increased, the output characteristics are deteriorated, and therefore, running performance of these vehicles is deteriorated, which is problematic. In other words, in order to obtain stable running performance of automobiles, batteries for these automobiles are demanded not only to have low initial DC resistance but also to have a small increase in DC resistance due to time degradation.

The invention has been made under the above circumstances.

An object of the invention is to provide a non-aqueous electrolyte solution for a secondary battery that enables obtaining a secondary battery that is excellent in output characteristics, and to provide a secondary battery that is excellent in output characteristics.

Solution to Problem

The configuration, operation, and effect of the invention will be described with a technical idea. However, the mechanism of operation includes estimation, and the correctness or incorrectness thereof does not limit the invention.

Means for Solving the Above Problems are as Follows

<1> A non-aqueous electrolyte solution for a secondary battery, comprising a boron compound represented by the following Formula (1):

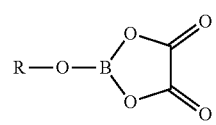

Formula (1)

wherein, in Formula (1), R represents an alkyl group having from 1 to 12 carbon atoms, an alkenyl group having from 2 to 12 carbon atoms, or a group represented by Formula (2):

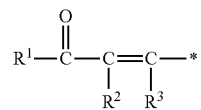

Formula (2)

wherein, in Formula (2), each of $R^1$ to $R^3$ independently represents a hydrogen atom, a halogen atom, an alkyl group having from 1 to 12 carbon atoms, an alkenyl group having from 2 to 12 carbon atoms, or an aryl group having from 6 to 12 carbon atoms, and * represents a bonding site with an oxygen atom in Formula (1).

<2> The non-aqueous electrolyte solution for a secondary battery according to <1>, wherein, in Formula (1), R is a group represented by Formula (2).

<3> The non-aqueous electrolyte solution for a secondary battery according to <1> or <2>, wherein a content of the boron compound represented by Formula (1) is from 0.01% by mass to 10% by mass based on a total amount of the non-aqueous electrolyte solution for a secondary battery.

<4> The non-aqueous electrolyte solution for a secondary battery according to any one of <1> to <3>, further comprising at least one compound selected from the group consisting of a carbonate compound having a carbon-carbon unsaturated bond or a fluorine atom, and a cyclic sulfonic acid ester.

<5> The non-aqueous electrolyte solution for a secondary battery according to any one of <1> to <3>, further comprising a carbonate compound having a carbon-carbon unsaturated bond or a fluorine atom, wherein a content of the carbonate compound having a carbon-carbon unsaturated bond or a fluorine atom is from 1% by mass to 15% by mass based on a total amount of the non-aqueous electrolyte solution for a secondary battery.

<6> The non-aqueous electrolyte solution for a secondary battery according to any one of <1> to <3> and <5>, further comprising a cyclic sulfonic acid ester, wherein a content of the cyclic sulfonic acid ester is from 0.1% by mass to 10% by mass based on a total amount of the non-aqueous electrolyte solution for a secondary battery.

<7> A secondary battery, comprising a positive electrode, a negative electrode, and the non-aqueous electrolyte solution according to any one of <1> to <6>.

<8> A secondary battery, comprising a positive electrode, a negative electrode, and the non-aqueous electrolyte solution according to any one of <1> to <6>, the secondary battery being obtained by charging and discharging.

Advantageous Effects of Invention

According to the invention, a non-aqueous electrolyte solution for a secondary battery that enables obtaining a secondary battery that is excellent in output characteristics, and a secondary battery that is excellent in output characteristics are provided.

BRIEF DESCRIPTION OF DRAWINGS

FIG. 2 is a schematic view showing one embodiment of a power storage device configured by assembling a plurality of secondary batteries of the invention.

DESCRIPTION OF EMBODIMENTS

Figure 1:
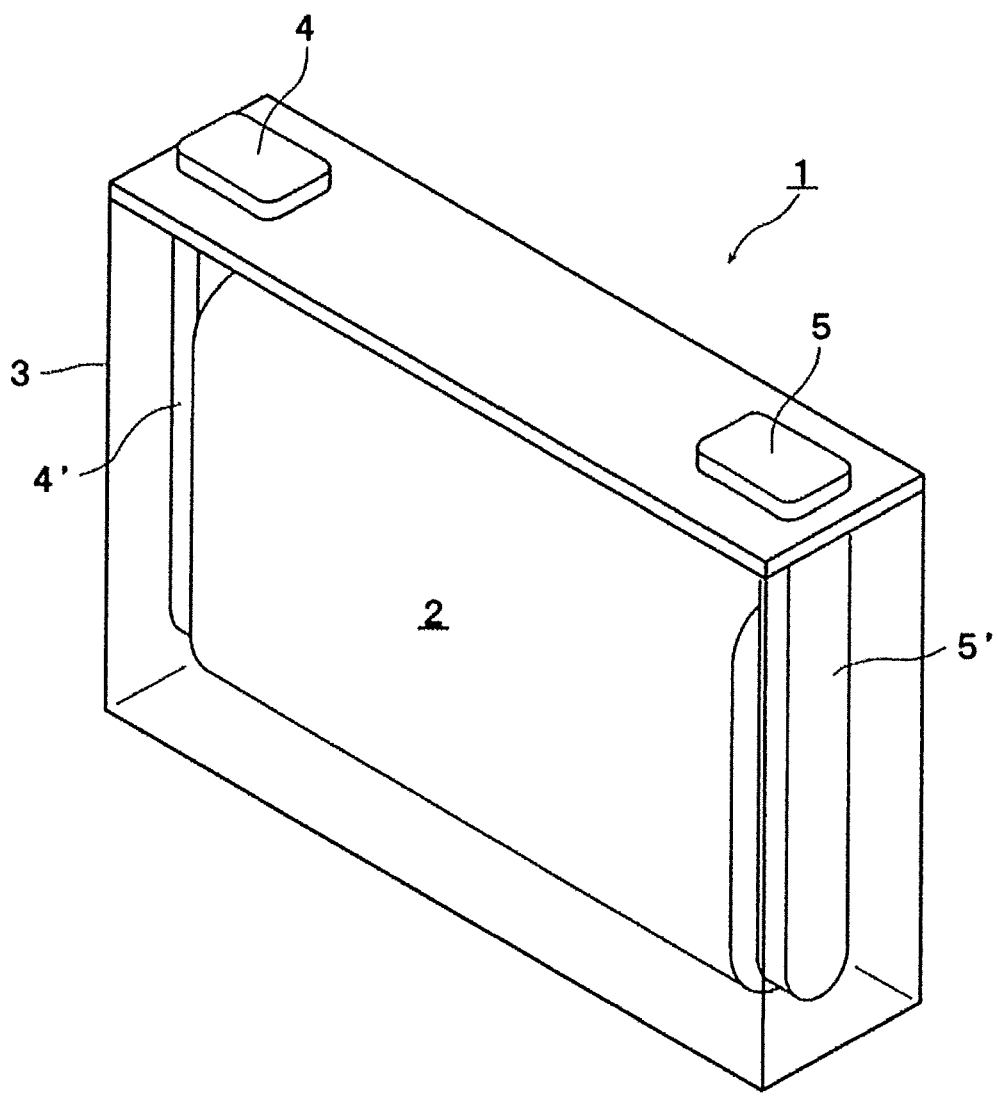
FIG. 1 is an external perspective view showing one embodiment of the secondary battery of the invention.

Embodiments of the invention will be described below. These descriptions and Examples are illustrative of the invention and do not limit the scope of the invention.

<Non-Aqueous Electrolyte Solution for Secondary Battery>

The non-aqueous electrolyte solution for a secondary battery (hereinafter, also simply referred to as "non-aqueous electrolyte solution") of the invention contains a boron compound represented by the following Formula (1).

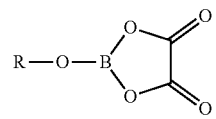

Formula (1)

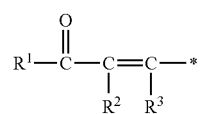

Formula (2)

In Formula (1), R represents an alkyl group having from 1 to 12 carbon atoms, an alkenyl group having from 2 to 12 carbon atoms, or a group represented by Formula (2). In Formula (2), $R^1$ to $R^3$ each independently represent a hydrogen atom, a halogen atom, an alkyl group having from 1 to 12 carbon atoms, an alkenyl group having from 2 to 12 carbon atoms, or an aryl group having from 6 to 12 carbon atoms, and * represents a bonding site with an oxygen atom in Formula (1).

Since the non-aqueous electrolyte solution of the invention contains a boron compound represented by Formula (1), when a secondary battery is manufactured, a secondary battery that is excellent in output characteristics (specifically, initial DC resistance reduction, and suppression of DC resistance increase due to time degradation) can be obtained. Although the detailed operational mechanism for obtaining such an effect is unknown, it is thought that the boron compound represented by Formula (1) is decomposed by the initial charging to generate an oxalato structure portion ".O—(C=O)$_2$—O.", which acts on the surface of an electrode (an active material), whereby an ion conduction path with high ion conductivity is formed. Among boron compounds, a boron compound having the structure represented by Formula (1) (and thereamong, particularly a boron compound having the substituent represented by Formula (2)) is considered to be advantageous from the viewpoint of decomposition to easily generate an oxalato structure portion. In the boron compound represented by Formula (1), an oxalato group and a group represented by R—O— are bonded to the boron atom as substituents, and since the boron compound has an asymmetric molecular structure around the boron atom, an imbalance is able to be caused in the charge distribution in the molecule, whereby, among boron compounds, such a boron compound is considered to be easily decomposed by initial charging, and to thereby effectively exhibit the above action.

Hereinafter, the components, compositions, and the like of the non-aqueous electrolyte solution of the invention will be described in detail.

[Boron Compound Represented by Formula (1)]

In Formula (1), R represents an alkyl group having from 1 to 12 carbon atoms, an alkenyl group having from 2 to 12 carbon atoms, or a group represented by Formula (2).

The alkyl group having from 1 to 12 carbon atoms represented by R is more preferably an alkyl group having from 1 to 10 carbon atoms, still more preferably an alkyl group having 1 to 8 carbon atoms, still more preferably an alkyl group having from 1 to 6 carbon atoms, and still more preferably an alkyl group having from 1 to 4 carbon atoms.

Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, and a tert-octyl group.

The alkyl group having from 1 to 12 carbon atoms represented by R may be unsubstituted or substituted with a halogen atom (for example, a fluorine atom, a chlorine atom) or the like.

The alkenyl group having from 2 to 12 carbon atoms represented by R is more preferably an alkenyl group having from 2 to 10 carbon atoms, still more preferably an alkenyl group having from 2 to 8 carbon atoms, still more preferably an alkenyl group having from 2 to 6 carbon atoms, and still more preferably an alkenyl group having from 2 to 4 carbon atoms.

Examples of the alkenyl group include an ethenyl group, a propenyl group, a butenyl group, a pentenyl group, a hexenyl group, a heptenyl group, and an octenyl group.

The alkenyl group having from 2 to 12 carbon atoms represented by R may be unsubstituted or substituted with a halogen atom (for example, a fluorine atom, a chlorine atom) or the like.

R is preferably a group represented by Formula (2). In Formula (2), $R^1$ to $R^3$ each independently represent a hydrogen atom, a halogen atom, an alkyl group having from 1 to 12 carbon atoms, an alkenyl group having from 2 to 12 carbon atoms, or an aryl group having from 6 to 12 carbon atoms.

Examples of the halogen atom represented by $R^1$ to $R^3$ include a fluorine atom, a chlorine atom, and a bromine atom, and a fluorine atom is preferable.

The alkyl group having from 1 to 12 carbon atoms represented by $R^1$ to $R^3$ is more preferably an alkyl group having from 1 to 10 carbon atoms, still more preferably an alkyl group having from 1 to 8 carbon atoms, still more preferably an alkyl group having from 1 to 6 carbon atoms, still more preferably an alkyl group having from 1 to 4 carbon atoms, and still more preferably an alkyl group having from 1 to 3 carbon atoms.

Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, and a tert-octyl group.

The alkyl group having from 1 to 12 carbon atoms represented by $R^1$ to $R^3$ may be unsubstituted or substituted with a halogen atom (for example, a fluorine atom, a chlorine atom) or the like.

The alkenyl group having from 2 to 12 carbon atoms represented by $R^1$ to $R^3$ is more preferably an alkenyl group having from 2 to 10 carbon atoms, still more preferably an alkenyl group having from 2 to 8 carbon atoms, still more preferably an alkenyl group having from 2 to 6 carbon atoms, and still more preferably an alkenyl group having from 2 to 4 carbon atoms.

Examples of the alkenyl group include an ethenyl group, a propenyl group, a butenyl group, a pentenyl group, a hexenyl group, a heptenyl group, and an octenyl group.

The alkenyl group having from 2 to 12 carbon atoms represented by $R^1$ to $R^3$ may be unsubstituted or substituted with a halogen atom (for example, a fluorine atom, a chlorine atom) or the like.

The aryl group having from 6 to 12 carbon atoms represented by $R^1$ to $R^3$ is more preferably an aryl group having from 6 to 10 carbon atoms.

Examples of the aryl group include a phenyl group, a group in which one hydrogen atom is removed from an alkylbenzene (for example, a benzyl group, a tolyl group, a xylyl group, or a mesityl group), a naphthyl group, and a group in which one hydrogen atom is removed from an alkyl-substituted naphthalene.

The aryl groups having from 6 to 12 carbon atoms represented by $R^1$ to $R^3$ may be unsubstituted, or substituted with a halogen atom (for example, a fluorine atom, or a chlorine atom) or the like.

In Formula (2), at least one of $R^1$ to $R^3$ is preferably an alkyl group, an alkenyl group, or an aryl group, and it is more preferable that at least two of $R^1$ to $R^3$ are an alkyl group, an alkenyl group, or an aryl group. Preferable embodiments of an alkyl group, an alkenyl group, and an aryl group in this case are as described above, and among an alkyl group, an alkenyl group, and an aryl group, an alkyl group is preferable.

Specific examples of the boron compound represented by Formula (1) include the following exemplified compounds (1) to (26).

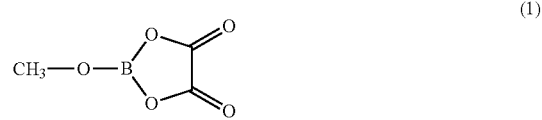

(1)

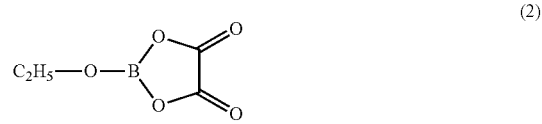

(2)

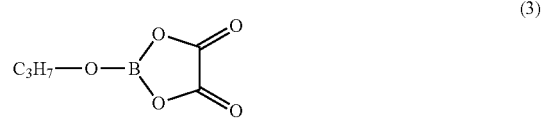

(3)

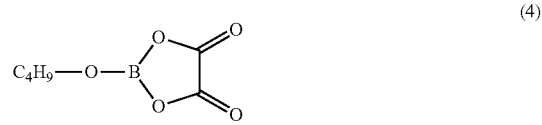

(4)

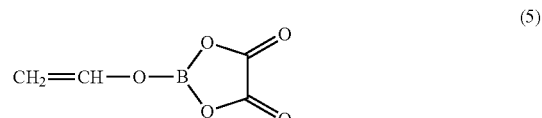

(5)

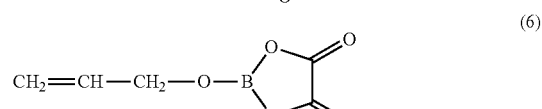

(6)

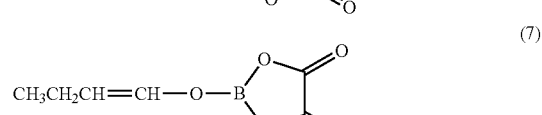

(7)

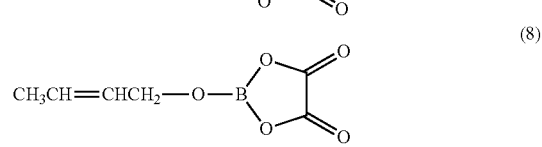

(8)

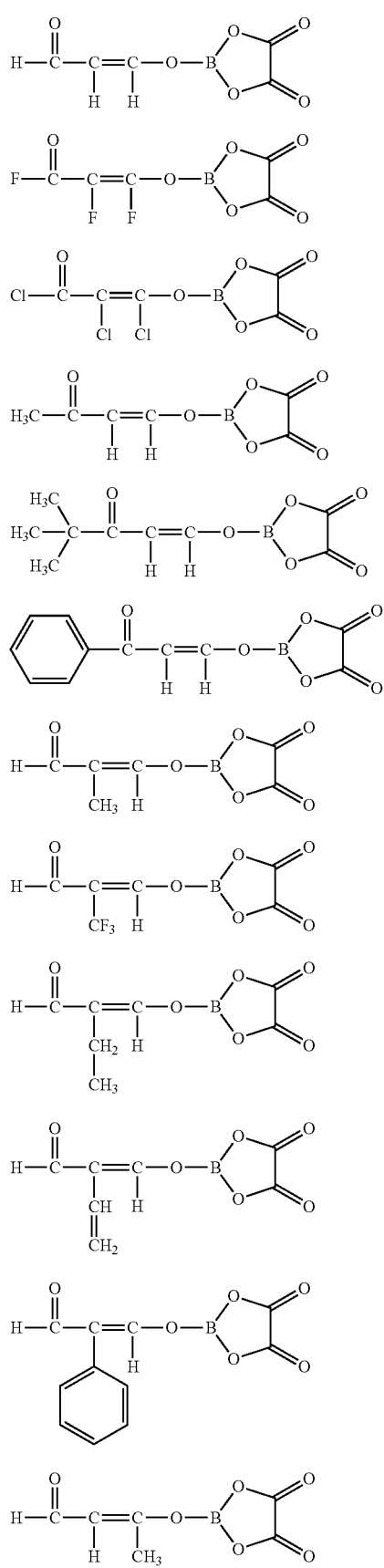

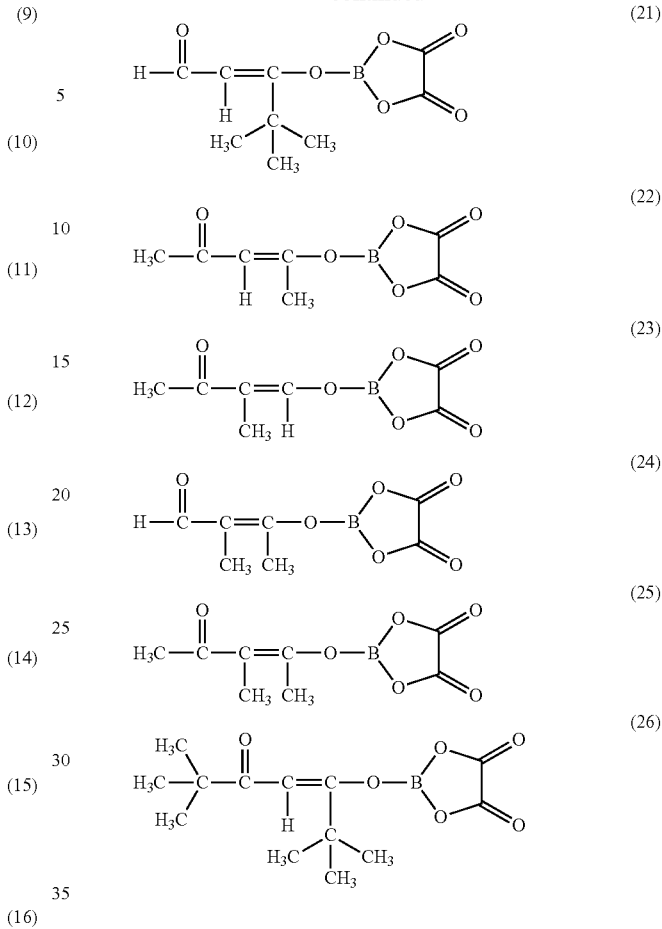

The boron compound represented by Formula (1) can be synthesized, for example, by the method described in Chemische Berichte, Volume 68, Issue 6, Pages 1949-55, 1965.

The content (total content in the case of two or more kinds) of the boron compound represented by Formula (1) is preferably from 0.01% by mass to 10% by mass based on the total amount of the non-aqueous electrolyte solution, more preferably from 0.05% by mass to 5% by mass, still more preferably 0.1% by mass to 5% by mass, still more preferably from 0.5% by mass to 5% by mass, still more preferably from 0.5% by mass to 3% by mass, still more preferably from 0.5% by mass to 2% by mass, and still more preferably from 0.5% by mass to 1% by mass.

The boron compound represented by Formula (1) may be used singly, or in mixture of two or more kinds thereof.

[Non-Aqueous Solvent]

As the non-aqueous solvent used in the non-aqueous electrolyte solution of the invention, a cyclic or linear aprotic solvent is preferable. Examples of the cyclic aprotic solvent include: a cyclic carbonate such as ethylene carbonate; a cyclic ester such as γ-butyrolactone; a cyclic sulfone such as sulfolane; and a cyclic ether such as dioxolane. Examples of the linear aprotic solvent include: a linear carbonate such as dimethyl carbonate; a linear carboxylic acid ester such as methyl propionate; and a linear ether such as dimethoxyethane. These solvents may be used singly, or in mixture of two or more kinds thereof.

When it is intended to improve the load characteristics and low temperature characteristics of a secondary battery, it is preferable to make the non-aqueous solvent into a mixture of a cyclic aprotic solvent and a linear aprotic solvent. Furthermore, from the viewpoint of the electrochemical stability of the non-aqueous electrolyte solution, it is preferable to use cyclic carbonate as a cyclic aprotic solvent and linear carbonate as a linear aprotic solvent.

Specific examples of the cyclic carbonate include ethylene carbonate, propylene carbonate, 1,2-butylene carbonate, trans-2,3-butylene carbonate, cis-2,3-butylene carbonate, 1,2-pentylene carbonate, trans-2,3-pentylene carbonate, and cis-2,3-pentylene carbonate. Among them, ethylene carbonate and propylene carbonate are preferable from the viewpoint of high dielectric constant. When graphite is used as a negative electrode active material, ethylene carbonate is preferable.

Specific examples of the linear carbonate include dimethyl carbonate, ethyl methyl carbonate, diethyl carbonate, methyl propyl carbonate, methyl isopropyl carbonate, dipropyl carbonate, methyl butyl carbonate, dibutyl carbonate, ethyl propyl carbonate, and methyl trifluoroethyl carbonate. Among them, dimethyl carbonate, ethyl methyl carbonate, and diethyl carbonate are preferable from the viewpoint of low viscosity.

Regarding the mixing ratio when cyclic carbonate and linear carbonate are mixed, cyclic carbonate:linear carbonate (volume ratio) is preferably from 5:95 to 70:30, and more preferably from 10:90 to 60:40. When the mixing ratio is within this range, since increase in the viscosity of the non-aqueous electrolyte solution can be suppressed and the degree of dissociation of the electrolyte can be increased, the conductivity of the non-aqueous electrolyte solution contributing to charging and discharging characteristics of a battery can be enhanced.

[Electrolyte]

As the electrolyte used in the non-aqueous electrolyte solution of the invention, all known compounds as an electrolyte can be used, and for example, a lithium salt may be used.

Specific examples of the lithium salt include $LiPF_6$, $LiBF_4$, $LiClO_4$, $LiAsF_6Li_2SiF_6$, $LiOSO_2C_kF_{(2k+1)}$ (k=an integer from 1 to 8), $LiN(SO_2F)_2$, $LiN(SO_2C_kF_{(2k+1)})_2$ (k=an integer from 1 to 8), $LiPF_n(C_kF_{(2k+1)})_{(6-n)}$ (n=an integer from 1 to 5, k=an integer from 1 to 8), $LiBF_nC_kF_{(2k+1)}$ (n=an integer from 1 to 3, k=an integer from 1 to 8), $LiB(C_2O_4)_2$ (lithium bis oxalyl borate), $LiBF_2(C_2O_4)$ (lithium difluorooxalyl borate), $LiPF_3(C_2O_4)$ (lithium trifluoro oxalyl phosphate); a lithium salt represented by the following Formula.

$$LiC(SO_2R^{11})(SO_2R^{12})(SO_2R^{13})$$

$$LiN(SO_2OR^{14})(SO_2OR^{15})$$

$$LiN(SO_2R^{16})(SO_2OR^{17})$$

In Formula, $R^{11}$ to $R^{17}$ are perfluoroalkyl groups having from 1 to 8 carbon atoms. $R^{11}$ to $R^{13}$ may be the same or different from each other. $R^{14}$ and $R^{15}$ may be the same or different from each other. $R^{16}$ and $R^{17}$ may be the same or different from each other.

As the lithium salt, $LiPF_6$, $LiBF_4$, $LiN(SO_2C_kF_{(2k+1)})_2$ (k=an integer from 1 to 8) are preferable.

The lithium salt concentration of the non-aqueous electrolyte solution of the invention is preferably from 0.1 mol/L to 3 mol/L, and more preferably from 0.5 mol/L to 2 mol/L.

The lithium salt may be used singly, or in mixture of two or more kinds thereof.

[Additive]

The non-aqueous electrolyte solution of the invention may contain known additives added to a non-aqueous electrolyte solution. The additive is preferably at least one compound selected from the group consisting of a carbonate compound having a carbon-carbon unsaturated bond or a fluorine atom and a cyclic sulfonic acid ester. The additive may be used singly, or in mixture of two or more kinds thereof.

Examples of the carbonate compound having a carbon-carbon unsaturated bond or a fluorine atom include a carbonate compound having a carbon-carbon unsaturated bond such as vinylene carbonate, dimethylvinylene carbonate, or divinyl carbonate; a carbonate compound having a fluorine atom such as fluoroethylene carbonate, difluoroethylene carbonate, or trifluoromethylethylene carbonate. Among them, vinylene carbonate and fluoroethylene carbonate are preferable.

The content (total content in the case of two or more kinds) of the carbonate compound having a carbon-carbon unsaturated bond or a fluorine atom is preferably from 1% by mass to 15% by mass based on the total amount of the non-aqueous electrolyte solution, and more preferably from 5% by mass to 10% by mass.

Examples of the cyclic sulfonic acid ester include 1,3-propane sultone, 1,4-butane sultone, 1,3-prop-1-ene sultone (also known as 1,3-propene sultone), 1-methyl-1,3-prop-1-ene sultone, 2-methyl-1,3-prop-1-ene sultone, and 3-methyl-1,3-prop-1-ene sultone, and among them, 1,3-prop-1l-ene sultone is preferable.

The content (total content in the case of two or more kinds) of the cyclic sulfonic acid ester is preferably from 0.1% by mass to 10% by mass based on the total amount of the non-aqueous electrolyte solution, more preferably from 0.5% by mass to 5% by mass, and still more preferably from 1% by mass to 5% by mass.

Examples of the other additives include a sulfur compound such as ethylene sulfite, propylene sulfite, ethylene sulfate, propylene sulfate, butene sulfate, hexene sulfate, vinylene sulfate, 3-sulfolene, divinyl sulfone, dimethyl sulfate, or diethyl sulfate; a vinyl boronic acid compound such as dimethyl vinyl boronate, diethyl vinyl boronate, dipropyl vinyl boronate, or dibutyl vinyl boronate; an amide such as dimethylformamide; a linear carbamate such as methyl-N,N-dimethylcarbamate; a cyclic amide such as N-methylpyrrolidone; a cyclic urea such as N,N-dimethylimidazolidinone; a boric acid ester such as trimethyl borate, triethyl borate, tributyl borate, trioctyl borate, or tri(trimethylsilyl) borate; a phosphoric acid ester such as trimethyl phosphate, triethyl phosphate, tributyl phosphate, trioctyl phosphate, tri(trimethylsilyl) phosphate, or triphenyl phosphate; an ethylene glycol derivative such as an ethylene glycol dimethyl ether, a diethylene glycol dimethyl ether, or a polyethylene glycol dimethyl ether; an aromatic hydrocarbon such as biphenyl, fluorobiphenyl, o-terphenyl, toluene, ethylbenzene, fluorobenzene, cyclohexylbenzene, 2-fluoroanisole, or 4-fluoroanisole; and a carboxylic acid anhydride having a carbon-carbon unsaturated bond such as a maleic anhydride or a norbornene dicarboxylic anhydride.

<Secondary Battery>

A secondary battery of the invention comprises a positive electrode, a negative electrode, and the non-aqueous electrolyte solution of the invention. An example of the secondary battery of the invention is a secondary battery in which a structure in which a negative electrode and a positive electrode are opposed to each other with a separator interposed therebetween is enclosed in an external packaging material together with the non-aqueous electrolyte solution of the invention. The secondary battery of the invention is preferably a lithium ion secondary battery that obtains electromotive force by doping/dedoping lithium ions. Hereinafter, constituent elements of the secondary battery of the invention will be described.

[Positive Electrode]

The positive electrode preferably has a structure in which an active material layer containing a positive electrode active material and a binder is formed on a current collector. The active material layer may further include a conductive aid.

As the positive electrode active material, a compound known as a positive electrode active material can be used. Specific examples of the positive electrode active material include a composite oxide represented by the composition formula $Li_xMO_2$ or $Li_yM_2O_4$ which is a compound capable of intercalating and deintercalating lithium (M is one or more kinds selected from transition metals, $0 \leq x \leq 1$, $0 \leq y \leq 2$); a polyanion compound represented by $Li_wMe_x(XO_y)_z$ (Me is at least one transition metal, X is P, Si, B, V, for example); and a metal chalcogenide or metal oxide having a tunnel structure and a layered structure. Specific examples thereof include $LiCoO_2$, $LiCo_{1/2}Ni_{1/2}O_2$, $Li_xNi_yMn_zCo_{(1-y-z)}O_2$, $LiMn_2O_4$, $Li_2Mn_2O_4$, $Li_xNi_yMn_{(2-y)}O_4$, $LiFePO_4$, $LiMnPO_4$, $LiNiPO_4$, $LiCoPO_4$, $Li_3V_2(PO_4)_3$, $Li_2MnSiO_4$, $Li_2CoPO_4F$, $MnO_2$, $FeO_2$, $V_2O_5$, $V_6O_{13}$, $TiO_2$, and $TiS_2$. An element or a polyanion in these compounds may be partially substituted with another element or an anionic species. Besides, examples of the positive electrode active material include a conductive polymer such as polyaniline, disulfide, polypyrrole, polyparastyrene, polyacetylene, or polyacene, and a pseudo graphitic structure carbonaceous material. The positive electrode active material may be used singly, or in mixture of two or more kinds thereof.

Examples of the binder include a polyvinylidene fluoride resin, a styrene butadiene rubber, and a carboxymethyl cellulose. Examples of the conductive aid include a carbonaceous material such as acetylene black, Ketjen black, or graphite powder. Examples of the current collector include an aluminum foil, a titanium foil, and a stainless steel foil.

[Negative Electrode]

The negative electrode preferably has a structure in which an active material layer containing a negative electrode active material and a binder is formed on a current collector. The active material layer may further include a conductive aid.

As the negative electrode active material, a compound known as a negative electrode active material can be used. As a negative electrode active material, a compound capable of occluding and releasing lithium is preferable. Specific examples include elemental lithium; an alloy of Al, Si, Pb, Sn, Zn, Cd or the like with lithium; a lithium-containing transition metal oxide such as $LiFe_2O_3$ or $Li_4TisO_{12}$; a metal oxide such as $WO_2$, $MoO_2$, SiO, CuO, or SnO; a carbonaceous material such as graphite or carbon; lithium nitride such as $Li_3N$; and a lithium-containing transition metal nitride. The negative electrode active material may be used singly, or in combination of two or more kinds thereof.

Examples of the binder include a polyvinylidene fluoride resin, a styrene butadiene rubber, and a carboxymethyl cellulose. Examples of the conductive aid include a carbonaceous material such as acetylene black, Ketjen black, or graphite powder. Examples of the current collector include a copper foil, a nickel foil, a stainless steel foil, and the like.

[Separator]

As the separator, it is preferable to use a woven fabric, a nonwoven fabric, a microporous film of a synthetic resin or the like, and among them, a microporous film of a synthetic resin is more preferable. As the microporous film of the synthetic resin, a microporous polyolefin film such as a microporous film of polyethylene or polypropylene, or a microporous film of combination thereof is preferable from the viewpoint of the thickness, film strength, film resistance and the like.

Besides, a porous solid electrolyte (for example, a porous polymer solid electrolyte membrane) and the non-aqueous electrolyte solution of the invention may be used in combination, and in this case, a porous solid electrolyte serves as a separator. A porous solid electrolyte and a microporous film of a synthetic resin may be used in combination.

The shape of the secondary battery of the invention is not particularly limited, and various shapes such as a square shape, an elongated cylindrical shape, a coin shape, a button shape, a sheet shape, and the like can be applied.

Hereinafter, an example of an embodiment of the invention will be described with reference to FIG. 1 and FIG. 2. FIG. 1 is an external perspective view showing a rectangular secondary battery which is an embodiment of the secondary battery of the invention. This drawing is taken through the inside of a container. FIG. 2 is a schematic diagram showing one embodiment of a power storage device including a plurality of secondary batteries of the invention.

In the secondary battery 1 shown in FIG. 1, an electrode group 2 is accommodated in a battery container 3. The electrode group 2 is formed by winding a positive electrode having a positive electrode active material and a negative electrode having a negative electrode active material with a separator interposed therebetween. The positive electrode is electrically connected to a positive electrode terminal 4 via a positive electrode lead 4' and the negative electrode is electrically connected to a negative electrode terminal 5 via a negative electrode lead 5'. The electrode group 2 is impregnated with the non-aqueous electrolyte solution of the invention.

The invention can also be realized as a power storage device including a plurality of the secondary batteries. The power storage device 30 shown in FIG. 2 includes a plurality of power storage units 20. Each of the power storage units 20 includes a plurality of secondary batteries 1. The electric power storage device 30 can be mounted as a battery for an automobile such as EV, HEV, or PHEV.

The secondary battery of the invention may be a secondary battery comprising a negative electrode, a positive electrode, and the non-aqueous electrolyte solution of the invention, and obtained by charging and discharging.

In other words, the secondary battery of the invention may be a secondary battery (charged and discharged secondary battery) prepared by first preparing a secondary battery before charging and discharging comprising a negative electrode, a positive electrode, and the non-aqueous electrolyte solution of the invention, and by then charging and discharging the secondary battery before charging and discharging at least once.

EXAMPLES

Hereinafter, the invention will be described in more detail with reference to Examples, but the invention is not limited to these Examples. The materials, amount of use, proportion, processing procedure and the like shown in the following Examples can be changed if appropriate without departing from the gist of the invention.

Example 1-1

[Preparation of Non-Aqueous Electrolyte Solution]

1.0 mol/L of $LiPF_6$ was dissolved in a mixed solvent in which ethylene carbonate (EC) and ethyl methyl carbonate (EMC) were mixed at a volume ratio of 30:70. A non-aqueous electrolyte solution was obtained by adding exemplified compound (25) ((3-methyl-2,4-pentanedionato) oxalatoborate) thereto. The concentration of the exemplified compound (25) was 0.5% by mass.

[Preparation of Secondary Battery]

A secondary battery of the type shown in FIG. 1 was manufactured using the non-aqueous electrolyte solution prepared above and the following positive electrode, negative electrode, and separator.

—Positive Electrode—

A positive electrode paste containing 93% by mass of a lithium transition metal composite oxide represented by $LiCo_{1/3}Ni_{1/3}Mn_{1/3}O_3O_2$ as a positive electrode active material, 3% by mass of acetylene black as a conductive aid, and 4% by mass of polyvinylidene fluoride (PVDF) as a binder and containing N-methyl-2-pyrrolidone as a dispersion solvent was obtained. This positive electrode paste was uniformly applied to an aluminum current collector having a thickness of 15 µm, dried, and press-formed by roll pressing to obtain a positive electrode.

—Negative Electrode—

A negative electrode paste containing 97% by mass of graphite as a negative electrode active material, 1% by mass of carboxymethyl cellulose as a binder, and 2% by mass of styrene butadiene rubber, and containing distilled water as a dispersion solvent was obtained. This negative electrode paste was uniformly coated on a copper current collector having a thickness of 10 µm, and dried, and then press-formed by roll pressing to obtain a negative electrode.

—Separator—

As the separator, a microporous polyethylene membrane having a thickness of 25 µm was used.

Comparative Example 1-1

A non-aqueous electrolyte solution and a secondary battery were prepared in the same manner as in Example 1-1 except that the exemplified compound (25) was not added.

Comparative Example 1-2

A non-aqueous electrolyte solution and a secondary battery were prepared in the same manner as in Example 1-1 except that the exemplified compound (25) was changed to trimethoxyborane (TMB).

Example 2-1, Comparative Examples 2-1 to 2-2

In Example 2-1 and Comparative Examples 2-1 and 2-2, non-aqueous electrolyte solutions and secondary batteries were prepared in the same manner as in Example 1-1 and Comparative Examples 1-1 to 1-2.

Example 3-1

[Preparation of Non-Aqueous Electrolyte Solution]

1.2 mol/L of $LiPF_6$ was dissolved in ethyl methyl carbonate (EMC). A non-aqueous electrolyte solution was obtained by adding fluoroethylene carbonate (FEC), 1,3-prop-1-ene sultone (PRS), and the exemplified compound (25) thereto. The FEC concentration was 7.5% by mass, the PRS concentration was 2% by mass, and the concentration of the exemplified compound (25) was 0.5% by mass.

[Preparation of Secondary Battery]

A secondary battery was prepared in the same manner as in Example 1-1 using the non-aqueous electrolyte solution prepared above.

Comparative Example 3-1

A non-aqueous electrolyte solution and a secondary battery were prepared in the same manner as in Example 3-1 except that the exemplified compound (25) was not added.

Example 4-1

[Preparation of Non-Aqueous Electrolyte Solution]

1.2 mol/L of $LiPF_6$ was dissolved in ethyl methyl carbonate (EMC). To the solution, fluoroethylene carbonate (FEC) and exemplified compound (25) were added to obtain a non-aqueous electrolyte solution. The FEC concentration was 7.5% by mass, and the concentration of the exemplified compound (25) was 0.5% by mass.

[Preparation of Secondary Battery]

A secondary battery was prepared in the same manner as in Example 1-1 using the non-aqueous electrolyte solution prepared above.

Examples 4-2 to 4-3

A non-aqueous electrolyte solution and a secondary battery were prepared in the same manner as in Example 4-1 except that the exemplified compound (25) was changed to an exemplified compound as shown in Table 4.

Comparative Example 4-1

A non-aqueous electrolyte solution and a secondary battery were produced in the same manner as in Example 4-1 except that the exemplified compound (25) was not added.

Example 5-1

In the same manner as in Example 4-1, a non-aqueous electrolyte solution and a secondary battery were prepared.

Examples 5-2 to 5-3

A non-aqueous electrolyte solution and a secondary battery were prepared in the same manner as in Example 5-1 except that the concentration of the exemplified compound (25) was changed as shown in Table 5.

Comparative Example 5-1

A non-aqueous electrolyte solution and a secondary battery were produced in the same manner as in Comparative Example 4-1.

<Performance Evaluation>

The performance of each of the secondary batteries of Examples and Comparative Examples was evaluated by performing the following tests. The results are shown in Tables 1 to 5.

[Initial DC Resistance]

First, two cycles of the initial charging and discharging process were carried out. The process was carried out at 25° C. Voltage control was performed on the voltage between the positive and negative terminals. In the first cycle, charging was performed at constant current and constant voltage charging for 8 hours at a current of 0.2 CmA, and a voltage of 4.20 V or 4.35 V, and discharging was performed at constant current discharging at a current of 0.2 CmA and a final voltage of 2.75 V. In the second cycle, charging was performed at constant current and constant voltage charging at a current of 1.0 CmA and a voltage of 4.20 V or 4.35 V for 3 hours, and discharging was performed at constant current discharging at a current of 1.0 CmA with a final voltage of 2.75 V. In all cycles, a pause time of 10 minutes was set after charging and after discharging. After discharging in the second cycle, the state of charge (SOC) of the battery was set to 50%, and then the battery was discharged at −20° C. at 0.2 CmA for 30 seconds, 0.5 CmA for 30 seconds, and then 1.0 CmA for 30 seconds. The relationship between the current and the voltage 10 seconds after the start of discharging at each discharging current was plotted, and the DC resistance was determined from the slope of a straight line obtained from plotting of 3 points. Relative values of the secondary batteries of Examples and other Comparative Examples were then calculated with the measured value of a secondary battery of Comparative Example including a non-aqueous electrolyte solution not containing a boron compound being regarded as 100. A lower relative value indicates that the DC resistance is smaller and the initial output characteristics are more excellent.

[High Rate Discharge Characteristics]

A test was carried out at 25° C. Voltage control was performed on the voltage between the positive and negative terminals. Charging was performed at constant current and constant voltage charging at a current of 1.0 CmA and a voltage of 4.20 V or 4.35 V for 3 hours, and discharging was performed at constant current discharging at a current of 5.0 CmA with a final voltage of 2.75 V. A pause time of 10 minutes was set after charging. The ratio (%) of the discharge capacity at 5 CmA to the discharge capacity at 1 CmA was calculated. The high ratio indicates that the high rate discharge characteristics are excellent.

[Low Temperature Discharge Characteristics]

Voltage control was performed on the voltage between the positive and negative terminals. Charging was performed at 25° C. at constant current and constant voltage charging at a current of 1.0 CmA and a voltage of 4.20 V or 4.35 V for 3 hours, and discharging was performed at −20° C. at constant current discharging at a current of 1.0 CmA with a final voltage of 2.75 V. A pause time of 5 hours at −20° C. was set after charging. The ratio (%) of the discharge capacity at −20° C. to the discharge capacity at 25° C. was calculated. The high ratio indicates that the low temperature discharge characteristics are excellent.

[Storage Characteristics]

All voltage control was carried out with respect to the voltage between the positive and negative electrode terminals. First, constant current and constant voltage charging at a current of 1.0 CmA, a voltage of 4.20 V or 4.35 V for 3 hours was performed at 25° C. Next, a battery was placed in an open circuit state, and stored in a constant temperature bath at 45° C. for 15 days. Next, constant current discharging at a current of 1.0 CmA with a final voltage of 2.75 V was performed at 25° C., and the discharge capacity was measured. After again performing constant current and constant voltage charging at 25° C. at a current of 1.0 CmA and a voltage of 4.20 V or 4.35 V for 3 hours, constant current discharging at a current of 1.0 CmA with a final voltage of 2.75 V was performed at 25° C., and the discharge capacity was measured. For each battery, the ratio of the discharge capacity (mAh) at the first cycle after storage at 45° C. to the initial discharge capacity (mAh) was calculated as "remaining capacity retention rate (%)", and the ratio of the discharge capacity (mAh) at the second cycle after storage at 45° C. to the initial discharge capacity (mAh) was calculated as "recovery capacity retention rate (%)". In this test, the discharge capacity at the second cycle in the initial charging and discharging process was defined as "initial discharge capacity (mAh)".

Further, after storage at 45° C. and after discharge at the second cycle, the DC resistance after storage was determined by the same method as the initial DC resistance. Relative values of the secondary batteries of Examples and other Comparative Examples were calculated with the measured value of the secondary battery of Comparative Example including a non-aqueous electrolyte solution not containing a boron compound being regarded as 100.

Higher remaining capacity retention rate and recovery capacity retention rate indicate that the storage characteristics are excellent. The DC resistance after storage indicates that the lower the relative value, the better the output characteristics.

TABLE 1

| | Boron compound | Initial DC resistance (−20° C.) | High rate discharge characteristics (5 C) | Low temperature discharge characteristics (−20° C.) | Storage characteristics (45° C., 15 days after) | | |
|---|---|---|---|---|---|---|---|
| | | | | | Remaining capacity retention rate | Recovery capacity retention rate | DC resistance after storage |
| Comparative Example 1-1 | — | 100 | 60% | 58% | 90% | 98% | 100 |
| Comparative Example 1-2 | 0.5% TMB | 92 | 57% | 52% | 78% | 93% | 110 |
| Example 1-1 | 0.5% exemplified compound (25) | 98 | 66% | 65% | 92% | 99% | 93 |

Non-aqueous electrolyte solution: 1.0 mol/L LiPF$_6$/EC:EMC (30:70)

Charging voltage: 4.20 V

TABLE 2

| | Boron compound | Initial DC resistance (−20° C.) | High rate discharge characteristics (5 C) | Low temperature discharge characteristics (−20° C.) | Storage characteristics (45° C., 15 days after) | | |
|---|---|---|---|---|---|---|---|
| | | | | | Remaining capacity retention rate | Recovery capacity retention rate | DC resistance after storage |
| Comparative Example 2-1 | — | 100 | 39% | 46% | 87% | 96% | 100 |
| Comparative Example 2-2 | 0.5% TMB | 99 | 44% | 41% | 70% | 87% | 125 |
| Example 2-1 | 0.5% exemplified compound (25) | 97 | 53% | 52% | 89% | 99% | 97 |

Non-aqueous electrolyte solution: 1.0 mol/L LiPF$_6$/EC:EMC (30:70)
Charging voltage: 4.35 V As shown in Tables 1 and 2, the initial DC resistance at −20° C. was lower in Examples 1-1 and 2-1 than in Comparative Examples 1-1 and 2-1. From this, it can be seen that even in the general voltage charging condition (charging voltage 4.20 V) and even in high voltage charging condition (charging voltage 4.35 V), addition of the boron compound represented by Formula (1) reduced the DC resistance of the secondary battery, in other words, the output characteristics of the secondary battery were improved.

In Examples 1-1 and 2-1, the DC resistance after storage at 45° C. was lower than that of Comparative Examples 1-1 and 2-1. From this, it can be seen that even in a general voltage charging condition (charging voltage 4.20 V) and even in a high voltage charging condition (charging voltage 4.35 V), addition of the boron compound represented by Formula (1) suppressed an increase in DC resistance due to time degradation of the secondary battery, in other words, the output characteristics of the secondary battery were improved.

Furthermore, as compared with Comparative Examples 1-1 and 2-1, Examples 1-1 and 2-1 were superior both in the remaining capacity retention rate and the recovery capacity retention rate after storage at 45° C. From this, it can be seen that even in a general voltage charging condition (charging voltage 4.20 V) and even in high voltage charging condition (charging voltage 4.35 V), the storage characteristics of a secondary battery are improved by addition of the boron compound represented by Formula (1).

On the other hand, in a case in which TMB was used as the boron compound (Comparative Example 1-2, Comparative Example 2-2), the remaining capacity retention rate, the recovery capacity retention rate, and the DC resistance after storage at 45° C. were inferior to those in the case of not containing a boron compound (Comparative Example 1-1, Comparative Example 2-1). Therefore, it cannot be said that addition of any boron compound to a non-aqueous electrolyte solution always improves the output characteristics and storage characteristics of a secondary battery. It can be said that the boron compound represented by Formula (1) exerts a special effect, which is unobtainable in TMB which is a boron compound conventionally known as an additive for non-aqueous electrolyte solution, with respect to the output characteristics and storage characteristics of a secondary battery.

Regarding high rate discharge characteristics and low temperature discharge characteristics, Example 1-1 is superior to Comparative Example 1-1, and Example 2-1 is superior to Comparative Example 2-1. From this, it can be seen that addition of the boron compound represented by Formula (1) also improves the discharge characteristics of a secondary battery. In addition, Example 1-1 is superior to Comparative Example 1-2, and Example 2-1 is superior to Comparative Example 2-2. From this, it can be seen that, regarding the discharge characteristics of the secondary battery, the boron compound represented by Formula (1) has an effect superior to that of TMB which is a boron compound conventionally known as an additive for a non-aqueous electrolyte solution.

TABLE 3

| | Boron compound | Initial DC resistance (−20° C.) | High rate discharge characteristics (5 C) | Low temperature discharge characteristics (−20° C.) | Storage characteristics (45° C., 15 days after) | | |
|---|---|---|---|---|---|---|---|
| | | | | | Remaining capacity retention rate | Recovery capacity retention rate | DC resistance after storage |
| Comparative Example 3-1 | — | 100 | 73% | 46% | 94% | 98% | 100 |
| Example 3-1 | 0.5% exemplified compound (25) | 97 | 82% | 48% | 94% | 98% | 94 |

Non-aqueous electrolyte solution: 1.2 mol/L LiPF$_6$/EMC + 7.5% FEC + 2% PRS
Charging voltage: 4.35 V As shown in Table 3, Example 3-1 was equivalent or superior in all evaluation items as compared with Comparative Example 3-1. From this, it can be seen that even when the boron compound represented by Formula (1) is used in combination with other additives (FEC and PRS), it does not adversely affect the battery performance of a secondary battery, and addition of the boron compound represented by Formula (1) improves the overall battery performance of a secondary battery.

TABLE 4

|  | Boron compound | Initial DC resistance (−20° C.) | Storage characteristics (45° C., 15 days after) | | |
|---|---|---|---|---|---|
|  |  |  | Remaining capacity retention rate | Recovery capacity retention rate | DC resistance after storage |
| Comparative Example 4-1 | — | 100 | 90% | 96% | 100 |
| Example 4-1 | 0.5% exemplified compound (25) | 94 | 91% | 97% | 93 |
| Example 4-2 | 0.5% exemplified compound (22) | 96 | 91% | 97% | 94 |
| Example 4-3 | 0.5% exemplified compound (26) | 94 | 88% | 96% | 96 |

Non-aqueous electrolyte solution: 1.2 mol/L LiPF$_6$/EMC + 7.5% FEC
Charging voltage: 4.35 V As shown in Table 4, in Examples 4-1 to 4-3, the initial DC resistance at −20° C. was lower than that of Comparative Example 4-1. From this, it can be seen that addition of various boron compounds represented by Formula (1) reduces the DC resistance of a secondary battery, in other words, the output characteristics of a secondary battery are improved.

Further, in Examples 4-1 to 4-3, the DC resistance after storage at 45° C. was lower than that of Comparative Example 4-1. From this, it can be seen that addition of various boron compounds represented by Formula (1) suppresses an increase in the DC resistance due to time degradation of a secondary battery, in other words, the output characteristics of a secondary battery are improved.

Further, Examples 4-1 to 4-2 were superior in all evaluation items as compared with Comparative Example 4-1. Among them, Example 4-1 using the exemplified compound (25) was the most excellent in any of the evaluation items. Therefore, among the boron compounds represented by Formula (1), the exemplified compound (25) and the exemplified compound (22) are preferable, and the exemplified compound (25) is more preferable.

boron compound represented by Formula (1) at various concentrations, the DC resistance of a secondary battery is reduced, in other words, the output characteristics of a secondary battery are improved.

In Examples 5-1 to 5-3, the DC resistance after storage at 45° C. was lower than that of Comparative Example 5-1. From this, it can be seen that by using the boron compound represented by Formula (1) at various concentrations, an increase in DC resistance due to time degradation of a secondary battery is suppressed, in other words, output characteristics of a secondary battery are improved.

When comparing the storage characteristics of Examples 5-1 to 5-3, the addition amount of the boron compound represented by Formula (1) is preferably 2% by mass or less, more preferably 1% by mass or less.

[Cycle Characteristics Test]

For each of the secondary batteries of Example 3-1 and Comparative Example 3-1, cycle characteristics tests of 200 cycles and 900 cycles were conducted.

Each cycle characteristics test was conducted at 45° C. Voltage control in each cycle characteristics test was performed on the voltage between positive and negative electrode terminals. In each cycle characteristics test, charging was performed at constant current and constant voltage charging at a current of 1.0 CmA, a voltage of 4.35 V for 3 hours, and discharging was performed at constant current

TABLE 5

|  | Boron compound | Initial DC resistance (−20° C.) | Storage characteristics (45° C., 15 days after) | | |
|---|---|---|---|---|---|
|  |  |  | Remaining capacity retention rate | Recovery capacity retention rate | DC resistance after storage |
| Comparative Example 5-1 | — | 100 | 90% | 96% | 100 |
| Example 5-1 | 0.5% exemplified compound (25) | 94 | 91% | 97% | 93 |
| Example 5-2 | 1% exemplified compound (25) | 97 | 92% | 98% | 91 |
| Example 5-3 | 2% exemplified compound (25) | 95 | 89% | 97% | 96 |

Non-aqueous electrolyte solution: 1.2 mol/L LiPF$_6$/EMC + 7.5% FEC
Charging voltage: 4.35 V As shown in Table 5, in Examples 5-1 to 5-3, the initial DC resistance at −20° C. was lower than that of Comparative Example 5-1. From this, it can be seen that by using the discharging at a current of 1.0 CmA with a final voltage of 2.75 V. In all the cycles, a pause time of 10 minutes was set after charging and after discharging.

After carrying out each cycle characteristics test, the thickness (hereinafter, also referred to as "battery thickness") of a secondary battery was measured with a caliper and the AC resistance (internal resistance) of a secondary battery was measured by an AC (1 kHz) impedance meter.

Table 6 shows the battery thickness (relative value) of Example 3-1 when the battery thickness of Comparative Example 3-1 was regarded as 100, and the AC resistance (relative value) of the secondary battery of Example 3-1 when the AC resistance of the secondary battery of Comparative Example 3-1 was regarded as 100.

After carrying out each cycle characteristics test, the capacity retention rate of the secondary battery was calculated. The results are shown in Table 6. Here, the capacity retention rate of the secondary battery was a discharge capacity (mAh) (relative value) in each cycle when the initial discharge capacity (mAh) described in the item of "storage characteristics" was regarded as 100.

TABLE 6

| | Boron compound | Cycle characteristics (after 200 cycles) | | | Cycle characteristics (after 900 cycles) | | |
|---|---|---|---|---|---|---|---|
| | | Capacity retention rate | AC resistance | Battery thickness | Capacity retention rate | AC resistance | Battery thickness |
| Comparative Example 3-1 | — | 95 | 100 | 100 | 71 | 100 | 100 |
| Example 3-1 | 0.5% exemplified compound (25) | 96 | 94 | 96 | 74 | 84 | 99 |

Non-aqueous electrolyte solution: 1.2 mol/L LiPF$_6$/EMC + 7.5% FEC + 2% PRS
Charging voltage: 4.35 V As shown in Table 6, in Example 3-1, the capacity retention rates after 200 cycles and after 900 cycles were higher than those in Comparative Example 3-1, and the AC resistance and the battery thickness after 200 cycles and after 900 cycles were small. From this, it can be seen that the addition of the boron compound represented by the Formula (1) also improves the cycle characteristics of the secondary battery.

The disclosure of Japanese Patent Application No. 2015-217704 is herein incorporated by reference in its entirety.

All documents, patent applications, and technical standards described in this specification are incorporated herein by reference to the same extent as if each individual document, patent application, or technical standard was specifically and individually indicated to be incorporated by reference.

The invention claimed is:

1. A non-aqueous electrolyte solution for a secondary battery, comprising a boron compound represented by the following Formula (1):

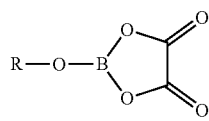

Formula (1)

wherein, in Formula (1), R represents an alkyl group having from 1 to 12 carbon atoms, an alkenyl group having from 2 to 12 carbon atoms, or a group represented by Formula (2):

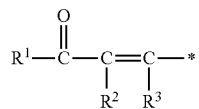

Formula (2)

wherein, in Formula (2), each of $R^1$ to $R^3$ independently represents a hydrogen atom, a halogen atom, an alkyl group having from 1 to 12 carbon atoms, an alkenyl group having from 2 to 12 carbon atoms, or an aryl group having from 6 to 12 carbon atoms, and * represents a bonding site with an oxygen atom in Formula (1).

2. The non-aqueous electrolyte solution for a secondary battery according to claim 1, wherein, in Formula (1), R is a group represented by Formula (2).

3. The non-aqueous electrolyte solution for a secondary battery according to claim 1, wherein a content of the boron compound represented by Formula (1) is from 0.01% by mass to 10% by mass based on a total amount of the non-aqueous electrolyte solution for a secondary battery.

4. The non-aqueous electrolyte solution for a secondary battery according to claim 1, further comprising at least one compound selected from the group consisting of a carbonate compound having a carbon-carbon unsaturated bond or a fluorine atom, and a cyclic sulfonic acid ester.

5. The non-aqueous electrolyte solution for a secondary battery according to claim 1, further comprising a carbonate compound having a carbon-carbon unsaturated bond or a fluorine atom, wherein a content of the carbonate compound having a carbon-carbon unsaturated bond or a fluorine atom is from 1% by mass to 15% by mass based on a total amount of the non-aqueous electrolyte solution for a secondary battery.

6. The non-aqueous electrolyte solution for a secondary battery according to claim 1, further comprising a cyclic sulfonic acid ester, wherein a content of the cyclic sulfonic acid ester is from 0.1% by mass to 10% by mass based on a total amount of the non-aqueous electrolyte solution for a secondary battery.

7. A secondary battery, comprising a positive electrode, a negative electrode, and the non-aqueous electrolyte solution for a secondary battery according to claim 1.

8. A secondary battery, comprising a positive electrode, a negative electrode, and the non-aqueous electrolyte solution for a secondary battery according to claim 1, the secondary battery being obtained by charging and discharging.

* * * * *